United States Patent
Yatsuka et al.

(10) Patent No.: US 6,894,034 B1
(45) Date of Patent: May 17, 2005

(54) SEBUM PRODUCTION INHIBITORS

(75) Inventors: Nobuaki Yatsuka, Ibaraki (JP);
Nobuyuki Sato, Ibaraki (JP);
Masazumi Nishikawa, Ibaraki (JP);
Tadakazu Tamai, Ibaraki (JP); Shigeru Moriyama, Ibaraki (JP)

(73) Assignee: Maruha Corporation, Tokyo (JP)

(*) Notice: Subject to any disclaimer, the term of this patent is extended or adjusted under 35 U.S.C. 154(b) by 1 day.

(21) Appl. No.: 10/089,179
(22) PCT Filed: Sep. 27, 2000
(86) PCT No.: PCT/JP00/06638
§ 371 (c)(1),
(2), (4) Date: Mar. 27, 2002
(87) PCT Pub. No.: WO01/22971
PCT Pub. Date: Apr. 5, 2001

(30) Foreign Application Priority Data

Sep. 27, 1999 (JP) ............................. 11-272022

(51) Int. Cl.$^7$ ............................. A61K 31/728
(52) U.S. Cl. ............................. 514/54; 536/53
(58) Field of Search ............................. 536/53; 514/54

(56) References Cited

U.S. PATENT DOCUMENTS 5,929,048 A * 7/1999 Falk et al. ............. 514/54

FOREIGN PATENT DOCUMENTS

| EP | 295082 A2 | 12/1988 |
|---|---|---|
| EP | 0 295 092 A2 | 12/1988 |
| EP | 1 074 631 A2 | 2/2001 |
| GB | 2207142 A * | 1/1989 |
| JP | 59-164712 | 9/1984 |
| JP | 07-101831 * | 4/1995 |
| JP | 10-279419 * | 10/1998 |
| JP | 11-236319 A | 8/1999 |
| JP | 11-310588 | 11/1999 |
| JP | 2000-103738 | 4/2000 |
| JP | 2000-191538 | 7/2000 |
| JP | 2000-191538 A | 7/2000 |
| WO | 85/04884 A1 | 11/1985 |
| WO | 99/57301 A1 | 11/1999 |

OTHER PUBLICATIONS

Webster's New World Dictionary, Simon & Schuster (1988), p. 38, entry for "alopecia."*

* cited by examiner

Primary Examiner—James O. Wilson
Assistant Examiner—Leigh C. Maier
(74) Attorney, Agent, or Firm—Birch, Stewart, Kolasch & Birch, LLP

(57) ABSTRACT

Sebum production inhibitors containing as an active ingredient a compound of general formula (1) below having a glucuronic acid derivative and a glucosamine derivative in the structure or a pharmacologically acceptable salt thereof

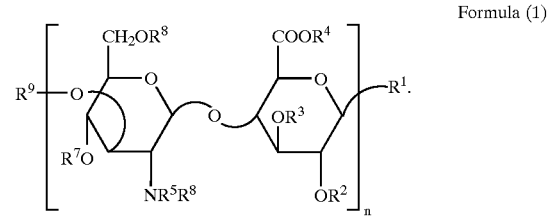

Formula (1)

6 Claims, No Drawings

SEBUM PRODUCTION INHIBITORS

This application is the national phase under 35 U.S.C. § 371 of PCT International Application No. PCT/JP00/06638 which has an International filing date of Sep. 27, 2000, which designated the United States of America.

TECHNICAL FIELD

The present invention relates to "sebum production inhibitors"containing as an active ingredient a compound having a glucuronic acid derivative and a glucosamine derivative in the structure.

BACKGROUND ART

The skin forms a thin sebaceous membrane on the surface of the epidermis. The sebaceous membrane plays the roles of preventing entry of outer foreign matters, protecting the skin against stimulation by various materials, smoothing the surface of the skin, inhibiting water evaporation, etc. However, it is known that excessive sebum is responsible for seborrheic diseases such as acne and dandruff. It is also known that sebum produces peroxides responsible for skin stimulation in the presence of UV rays or the like.

Acne is a typical seborrheic disease that is a skin disease mostly affecting teenagers and scientifically called acne vulgaris. It is clinically defined as "chronic inflammatory lesion prevailing the pilosebaceous systems". Acne has not been etiologically explained yet, but it is considered as a skin disease caused by complex combination of various factors, among which excessive sebum production, keratinization at the follicle and follicular bacteria are generally thought to have important roles (for example, Yamamoto Ayako: "Guidelines for Current Therapy, 1994 (Volume 36)", p. 632, Igaku-Shoin, Tokyo (1994)). Thus, common remedies for acne are external preparations containing sebum production inhibitors, keratolytic agents, antibacterials, lipase inhibitors and the like depending on the causative factor. However, acne remedies containing existing active ingredients have various disadvantages. For example, female hormones having a sebum production inhibitory effect inhibit epidermal growth to decrease sebum production, but hormone preparations induce undesirable side effects. Sulfur compounds such as sulfur and selenium disulfide representative of keratolytic agents do not show the hormone-like side effects, but often stimulate or dehydrate the skin during chronic use. Antibacterials such as hexachlorophenone, trichlorocarbanide and benzalkonium chloride show very high in vitro antimicrobial activity against the normal skin commensal, *Propionibacterium acnes*, but often show disappointing effects when they are actually used to treat acne in creams or ointments. Lipase inhibitors such as Ibuprofenpiconol or plant extracts such as peony or coptis root are not sufficiently effective for treating acne when they are formulated alone into creams or ointments.

A typical seborrheic disease in the scalp is increased dandruff. Excessive sebum is also considered to cause alopecia (Harada Shotaro: "Guidelines for Current Therapy, 1994 (Volume 36)", p. 633, Igaku-Shoin, Tokyo (1994); Watanabe Yasushi et al.: "Health Science, Diagnosis List for Hair", p. 1. Japan Hair Science Association, Tokyo (1993)). It is thought that alopecia caused by increased dandruff or excessive sebum can be treated or prevented by inhibiting sebum production.

Excessive sebum production is also known to cause cosmetic problems such as rough skin, shiny skin and greasy skin or hair.

It is known that the causative agents for increased human body odor associated with aging are also derived from sebum (Asahi Shimbun (morning edition): Aug. 30, 1999, p. 25). Any substances inhibiting sebum production may also control emission of the body odor associated with aging.

We already showed that compounds of the present invention have a platelet adhesion/aggregation suppressing effect in Japanese Patent Application No. 120425/1998 (JPA No. 310588/1999), a vascular endothelial cell growth promoting effect in Japanese Patent Application No. 273895/1998 (JPA No. 10.3738/2000) and a leukocyte-vascular endothelial cell adhesion suppressing effect in Japanese Patent Application No. 372B64/1998 (JPA No. 191538/2000). However, any sebum production inhibitory effect has not been disclosed.

As evident from the above description, it is a medically and cosmetically important object to provide an excellent sebum production inhibitor.

DISCLOSURE OF THE INVENTION

As a result of careful studies to solve the above problems, we accomplished the present invention on the basis of the finding that compounds of general formula (i) or pharmacologically acceptable salts thereof have an excellent sebum production inhibitory effect.

Accordingly, the present invention provides sebum production inhibitors containing as an active ingredient a compound of general formula (1) having a glucuronic acid derivative and a glucosamine derivative in the structure or a pharmacologically acceptable salt thereof.

Sebum production inhibitors of the present invention are useful as therapeutic or prophylactic agents for diseases caused by excessive sebum production. They are also useful as cosmetics for solving cosmetic problems caused by excessive sebum production. They are also useful as deodorants for the body odor associated with aging.

THE MOST PREFERRED EMBODIMENTS OF THE INVENTION

Compounds used in sebum production inhibitors of the present invention are compounds of general formula (1) below having a glucuronic acid derivative and a glucosamine derivative in the structure or pharmacologically acceptable salts thereof.

Formula (1)

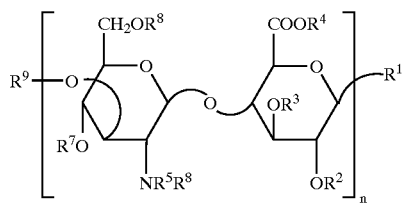

where $R^1$ denotes a protective group or any of formulae (2) to (5) below where $R^{10}$ denotes a hydrogen atom, a protective group or any of formulae (6) to (8) below, and $R^{11}$ denotes a hydrogen atom or a protective group, provided that when $R^{10}$ and $R^{11}$ are a hydrogen atom or a protective group, $R^1$ may be attached at the trans- or cis-position with respect to $COOR^4$, —OR$^{10}$      Formula (2)

—NHR$^{11}$,      Formula (3)

—CH$_2$R$^{11}$,      Formula (4)

—SR$^{11}$,      Formula (5)

Formula (6)

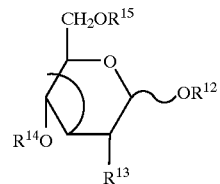

Formula (7)

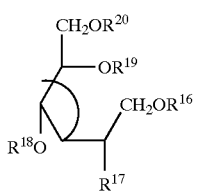

Formula (8)

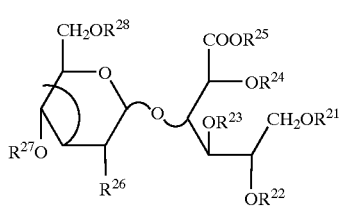

or when R$^{10}$ is any of formulae (6) to (8), R$^{12}$ to R$^{26}$ except R$^{13}$, R$^{17}$ and R$^{26}$ in formulae (6) to (8) are the same or different and denote a hydrogen atom or a protective group, and R$^{13}$, R$^{17}$ and R$^{26}$ denote an azido group or formula (9) below —NR$^{29}$R$^{30}$      Formula (9)

where R$^{29}$ and R$^{30}$ are the same or different and denote a hydrogen atom or a protective group, R$^2$ to R$^8$ are the same or different and denote a hydrogen atom or a protective group, R$^9$ denotes a hydrogen atom, a protective group or formula (10) or (11) below Formula (10)

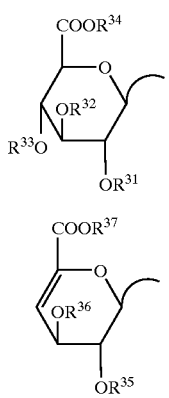

Formula (11)

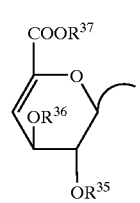

where R$^{31}$ to R$^{37}$ are the same or different and denote a hydrogen atom or a protective group, and n denotes an integer of 0 to 25, provided that when n is 0, R$^1$ is a group of formula (2). R$^{10}$ is a group of formula (8), and R$^9$ is a group of formula (10) or (11), with the proviso that in formulae (1), (6) to (8), and (10) to (11), the protective groups are the same or different and denote an optionally substituted straight or branched alkyl having 1 to 8 carbon atoms, an optionally substituted straight or branched alkenyl having 2 to 8 carbon atoms, an optionally substituted acyl having 1 to 8 carbon atoms, an optionally substituted aromatic acyl, or an optionally substituted aromatic alkyl, or any two protective groups of R$^2$ to R$^{37}$ except R$^{13}$, R$^{17}$ and R$^{26}$ may be combined to form an optionally substituted alkylidene having 3 to 8 carbon atoms, an optionally substituted cyclic alkylidene having 3 to 8 carbon atoms, optionally substituted benzylidene or optionally substituted phthaloyl, and when n is 2 or more, R$^2$ to R$^8$ may be the same or different in each recurring unit.

That is, compounds of formula (1) contained as active ingredients in sebum production inhibitors of the invention have a structure comprising a D-glucosamine derivative of formula (12) below and a D-glucuronic acid derivative of formula (13) below combined together.

Formula (12)

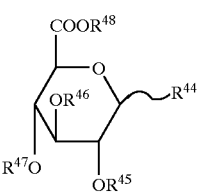

where R$^{38}$ to R$^{43}$ denote a hydrogen atom or a protective group.

Formula (13)

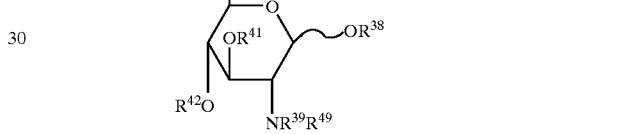

where R$^{44}$ denotes a hydroxyl group or a protective group, and R$^{45}$ to R$^{18}$ denote a hydrogen atom or a protective group.

In formula (1), n denotes an integer of 0 to 25, provided that when n is 0, R$^1$ is a group of formula (8) and R$^9$ is a group of formula (10) or (11). That is, compounds of formula (1) are represented by formula (14) or (15) below.

Formula (14)

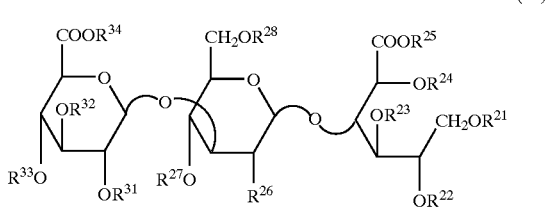

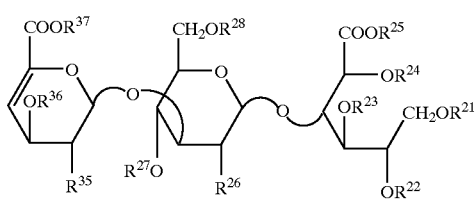

Formula (15)

As used herein, the protective group includes various protective groups shown in Theodra W. Green: "Productive Groups in Organic Synthesis"; 2nd Ed.; 1991.

The protective groups shown in formulae (1) to (11) above include optionally substituted straight or branched alkyls having 1 to 8 carbon atoms such as methyl, ethyl, propyl, isopropyl, butyl, tertiary butyl, pentyl, octyl, methoxymethyl, tertiary butylthiomethyl, 1-ethoxyethyl, siloxymethyl or 2-methoxyethoxymethyl; optionally substituted straight or branched alkenyls having 2 to 8 carbon atoms such as ethenyl, 1-propenyl, 2-propenyl, butenyl or octenyl: optionally substituted straight or branched acyls having 1 to 8 carbon atoms such as formyl, acetyl, propionyl, butyryl, valeryl or pivaloyl, or haloacyls including chloroacetyl, dichloroacetyl, trichloroacetyl and trifluoroacetyl; optionally substituted aromatic acyls such as benzoyl or parachlorobenzoyl; optionally substituted aromatic alkyls such as optionally substituted benzyl (e.g., 4-methoxybenzyl), optionally substituted diphenylmethyl or optionally substituted triphenylmethyl. As for the protective groups shown in formulae (1) to (11), any two protective groups of $R^2$ to $R^{37}$ except $R^{13}$, $R^{17}$ and $R^{26}$ may be combined to form a protective group, i.e., suitable protective groups further include optionally substituted alkylidenes having 3 to 8 carbon atoms such as propylidene, butylidene or octylidene; optionally substituted cyclic alkylidenes having 3 to 8 carbon atoms such as cyclopentylidene, cyclohexylidene or cycloheptylidene; and optionally substituted benzylidene or optionally substituted phthaloyl. Preferred protective groups for hydroxyl group include optionally substituted straight or branched acyls having 1 to 8 carbon atoms, optionally substituted aromatic alkyls, optionally substituted straight or branched alkenyls having 2 or more carbon atoms, or optionally substituted benzylidene, more preferably acetyl, benzyl, 1-propenyl or benzylidene. Preferred protective groups for amino group include optionally substituted straight or branched acyls having 1 to 8 carbon atoms or optionally substituted phthaloyl, more preferably acetyl or phthaloyl. Preferred protective groups for carboxyl group include optionally substituted straight or branched alkyls having 1 to 8 carbon atoms or optionally substituted aromatic alkyls, more preferably methoxyl, methyl, ethyl, propyl, isopropyl, butyl, isobutyl, pentyl, isopentyl or diphenylmethyl. The protective groups mentioned above may be the same or different in the same compound, and can be selected arbitrarily.

In formula (1), n is an integer of 0 to 25, preferably 0 to 10, more preferably 0 to 5, most preferably 2 to 4.

$R^9$ may be as defined above, and is preferably represented by formula (11). That is, compounds of formula (1) are preferably represented by formula (16) below.

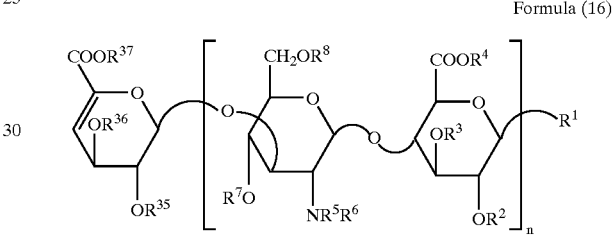

Formula (16)

More preferably, $R^1$ in formula (11) is represented by any of formulae (6) to (8), i.e., compounds are represented by any of formulae (17) to (19) below.

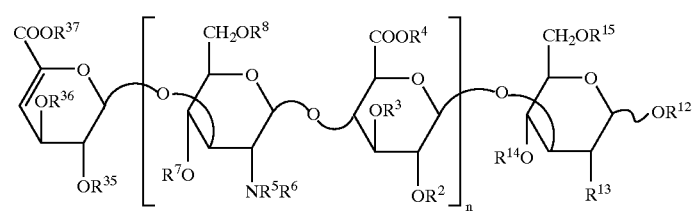

Formula (17)

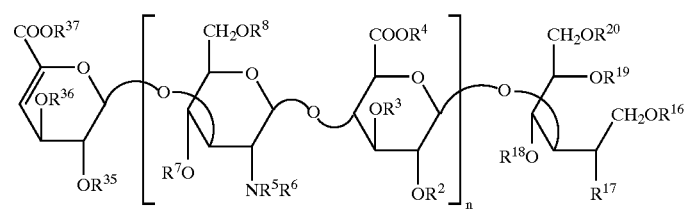

Formula (18)

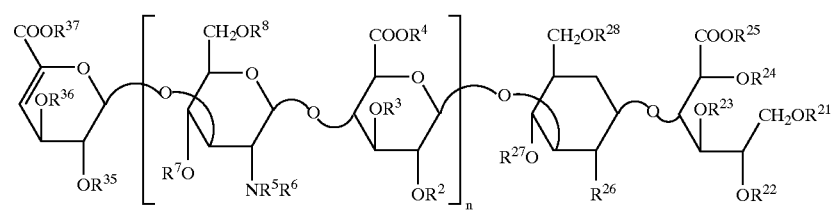

Formula (19)

Most preferably, $R^{13}$, $R^{17}$ and $R^{26}$ in formulae (17) to (19) above are represented by formula (9) above.

As used herein, the pharmacologically acceptable salt refers to a salt that has no adverse influence in vivo when a compound of the invention is administered in a therapeutically or prophylactically necessary amount, or a salt that does not lose pharmacologically effective properties of a compound of the invention. Specific examples are salts of alkali or alkali earth metals such as sodium salts, potassium salts or calcium salts; hydrohalogenic acid salts such as hydrofluorides, hydrochlorides, hydrobromides and hydrolodides; lower alkylsulfonates such as methanesulfonates, trifluoromethanesulfonates and ethanesulfonates; arylsulfonates such as benzenesulfonates and p-toluenesulfonates; organic acid salts such as fumarates, succinates, citrates, tartrates, oxalates and maleates; and amino acid salts such as glutamates and aspartates. Compounds of the invention and their salts also include solvates with various pharmacologically acceptable solvents such as water, organic solvents and buffers, or polymorphic forms.

Compounds of formula (1) may have an asymmetric carbon atom, depending on the type of the substituent, and may exist as optical isomers based on the presence of the asymmetric center. Thus, compounds of the present invention include all of individual isomers and their mixtures. For example, mixtures of an optical isomer and its enantiomer, especially racemic modifications consisting of a mixture of equal amounts of D and L isomers, or mixtures of an optical isomer and its diastereomer are included.

[Methods for Producing Compounds of Formula (1)]

Needless to say, various methods are available for obtaining compounds used in sebum production inhibitors of the invention. Examples of such methods are organic chemical methods, namely methods of synthesizing or modifying intermediates or desired compounds by organic chemical techniques using glucuronic acid derivatives and glucosamine derivatives as starting materials, or methods of obtaining intermediates or desired compounds by decomposing polysaccharides with acids or alkalis; biochemical methods, namely methods of synthesizing or modifying intermediates or desired compounds by utilizing reverse reactions of transferases or depolymerization enzymes with the use of glucuronic acid and N-acetylglucosamine as starting materials, or methods of obtaining intermediates or desired compounds by depolymerizing polysaccharides with enzymes; and genetic engineering methods, namely methods of obtaining starting materials, intermediates or desired compounds, or enzymes for use in synthesis or modification, by introduction of genes for enzymes into microorganisms or cells. These methods are used alone or in combination.

Preferred processes for preparing compounds of formula (1) are described in detail in Japanese Patent Application No. 120425/1998 (JPA No. 310588/1999) mentioned above.

[Sebum Production Inhibitors of the Present Invention and Administration Modes, Doses and Dosage Forms Thereof]

Sebum production inhibitors of the present invention contain as an active ingredient at least one of compounds of formula (1) or pharmacologically acceptable salts thereof.

When sebum production inhibitors of the present invention are used as medicines or cosmetics, they are normally administered systemically or locally, orally or parenterally. The dose is not specifically limited but should be optimally determined on the basis of overall judgment depending on various factors such as the type of the disease, the severity of the condition, the age and body weight of the subject to be treated. However, the daily dose is normally 0.01 to 100 mg/kg orally or 0.001 to 10 mg/kg parenterally per adult. The dose is administered once daily or divided into subdoses depending on the purpose.

Compounds of the present invention may be administered orally in the form of solid compositions, liquid compositions and other compositions or parenterally in the form of injections, external preparations and suppositories, and an optimal administration mode is selected depending on the purpose. Pharmaceutical compositions containing as an active ingredient at least one of compounds of the present invention and pharmacologically acceptable salts thereof can be prepared by using carriers, excipients and other additives used for ordinary formulation. Suitable carriers and excipients for formulation include., for example, lactose, magnesium stearate, starch, talc, gelatin, agar, pectin, acacia, olive oil, sesame oil, cacao butter, ethylene glycol and other common additives.

Suitable solid compositions for oral administration include tablets, pills, capsules, powders and granules. In such solid compositions, at least one active substance (active ingredient) is mixed with at least one inert diluent, such as lactose, mannitol, glucose, hydroxypropylcellulose, microcrystalline cellulose, starch, polyvinylpyrrolidone, or magnesium aluminometasilicate. The compositions may conventionally contain additives other than inert diluents, for example, lubricants such as magnesium stearate, disintegrants such as calcium carboxymethylcellulose, and solubilizers such as glutamic acid or aspartic acid. Tablets or pills may, if desired, be coated with a sugar coating or a gastric or enteric film comprising sucrose, gelatin, hydroxypropyl methylcellulose phthalate or the like or may be coated with two or more layers. Capsules of an absorbable material such as gelatin are also included.

Liquid compositions for oral administration include pharmaceutically acceptable emulsions, solutions, suspensions, syrups and elixirs, and may contain ordinary inert diluents, such as purified water and ethanol. In addition to inert diluents, these compositions may contain adjuvants such as wetting agents or suspending agents, sweetening agents, flavoring agents, aromatics and preservatives.

Injections for parenteral administration include sterile aqueous or nonaqueous solutions, suspensions and emulsions. Aqueous solutions and suspensions contain water for injection and physiological saline for injection, for example. Nonaqueous solutions and suspensions contain propylene glycol, polyethylene glycol, vegetable oils such as olive oil, alcohols such as ethanol, and POLYSORBATE 80 (registered trademark). These compositions may further contain adjuvants, such as preservatives, wetting agents, emulsifying agents, dispersing agents, stabilizers (e.g., lactose), and solubilizers (e.g., glutamic acid and aspartic acid). These can be sterilized by ordinary sterilizing methods, such as mechanical sterilization with a microfiltration membrane, heat sterilization such as autoclaving or inclusion of a bactericide. It is also possible to prepare a sterile solid composition and dissolve it in sterile water or a sterile solvent for injection before use.

Pharmaceutical compositions for parenteral administration or cosmetics include liquid preparations for external use, ointments, liniments, suppositories, transdermal preparations and ophthalmic solutions containing at least one of compounds of the present invention as an active ingredient. They can also be used in the form of oil-absorbing sheets or films. Formulations and preparation processes of various forms of cosmetics are described in known documents such as "Modern Cosmetic Science" (edited by Cosmetic Science Institute, Yakuji Nippo, 1980).

[Sebum Synthesis Inhibitory Effect of Compounds of Formula (1)]

Compounds of the present invention (Compound Nos. 1–10) were evaluated for sebum production inhibitory effect on hamster auricular skin tissue sections containing sebaceous glands. As a result, the compounds of the present invention showed an excellent sebum production inhibitory effect.

INDUSTRIAL APPLICABILITY

Compounds of formula (1) and pharmacologically acceptable salts thereof have an excellent sebum synthesis inhibitory effect so that they are useful as therapeutic and prophylactic agents based on such an effect. Specifically, they are useful as therapeutic and prophylactic agents for acne, dandruff, alopecia, etc.

They are also useful as ingredients of cosmetics. Specifically, they are useful as cosmetics for preventing rough skin, shiny skin, greasy skin or hair, the body odor associated with aging, etc.

EXAMPLES

The following examples further illustrate the present invention by way of Compound Production Examples, Test Examples for Sebum Production Inhibitory Effect, and Preparation Examples of Formulations and Cosmetics. As a matter of course, the invention is not limited to the materials and formulations described in the following examples, but includes all the materials and formulations included in the scope of claims.

Example 1

Compound Production Example 1

Production of 4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranose [ΔHexA β1→3GlcNAc β1→4GlcA β1→3GlcNAc (Compound Example 1)], 4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranose [ΔHexA β1→3GlcNAc β1→4GlcA β1→3GlcNAc β1→4GlcA β1→3GlcNAc (Compound Example 2)], 4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranose [ΔHexA β1→3GlcNAc β1→4GlcA β1→3GlcNAc β1→4GlcA β1→3GlcNAc β1→4GlcA β1→3GlcNAc (Compound Example 3)], and 4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranose [ΔHexA β1→3GlcNAc β1→4GlcA β1→3GlcNAc β1→4GlcA β1→3GlcNAc β1→4GlcA β1→3GlcNAc β1→4GlcA β1→3GlcNAc (Compound Example 4)]

A solution of 30 g of sodium hyaluronate (a product of KIBUN FOOD CHEMIFA; trade name "Hyaluronic acid FCH") dissolved in 3L of distilled water was heated to 40° C. The solution was adjusted to pH 6.0 with 0.1 M aqueous sodium hydroxide solution, and then a hyaluronidase derived from *Streptomyces hyalurolyticus* (a product of Amano Pharmaceutical; trade name "Hyaluronidase "Amano"") was added to decrease 0.5 turbidity units per mg of sodium hyaluronate, and the mixed solution was reacted for 100 hours at 40° C. After the reaction, the enzyme was removed from the solution by an ultrafiltration membrane (a product of Millipore) of hydrophilic polyether sulfone with a nominal molecular weight cutoff of 10k. The solvent was removed by lyophilization to give a depolymerization product (27.4 g).

The depolymerization product was fractionated by anion exchange chromatography (column: YMC-Pack IEC-AX, eluent A: water, B: 0.4M NaCl; linear gradient (30 min), detection: UV (232 nm)) (Compound Examples 1, 2, 3 and 4 were eluted in this order) to obtain fractions containing Compound Examples 1 to 4. Each fraction was desalted by gel filtration (gel: Sephadex G-10, eluent: water), and then lyophilized to obtain Compound Nos. 1 to 4 (white powder). Yields: Compound Example 1: 1.7 g, Compound Example 2: 5.9 g, Compound Example 3: 3.4 g, Compound Example 4: 2.2 g. Each compound was obtained as a sodium salt.

Compound Examples 1 to 4 are represented by formula (20) below where n denotes an integer of 1 to 4, i.e., n is 1, 2, 3 and 4, respectively.

Formula (20)

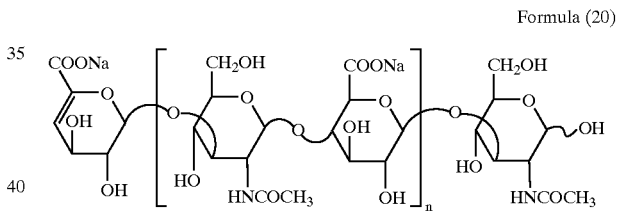

The purity of each compound measured by high performance liquid chromatography (column: TSKgel DEAE-5PW, eluent A: water, B: 0.3M NaCl; linear gradient (20 min), detection: UV (232 nm); area percentage method) was 97% or more. For each compound, the uronic acid content analyzed by the method of Bitter and Muir (Bitter, T., Muir, H.: Anal. Biochem., 4. 330 (1962)) using glucuronolactone as a standard and the hexosamine content analyzed by the method of Boas (without resin treatment; Boas, N., F.: J. Biol. Chem., 204, 553 (1953).) using glucosamine hydrochloride as a standard after hydrolysis at 100° C. for 16 hours in 3N hydrochloric acid nearly agreed with the theoretical values.

Example 2

Compound Production Example 2

Production of 4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranose [ΔHexA β1→3GlcNAc β1→4GlcA β1→3GlcNAc (Compound Example 1)], and 4-deoxy-α-L-threo-hexa-4-enepyranuronosyl-(1→3)-O-2-acetamide-2-deoxy-β-D-glucopyranosyl-(1→4)-3-O-β-D-glucopyranuronosyl- (1→3)-O-2-acetamide-2-deoxy-β-D-glucopyranosyl-(14)-3-O-β-D-glucopyranuronosyl-(1→3)-O-2-acetamide-2-deoxy-β-D-glucopyranose [ΔHexA 1→3GlcNAc β1→4GlcA β1→3GlcNAc β1→4GlcA β1→3GlcNAc (Compound Example 2)]

A solution of 60 g of sodium hyaluronate (a product of KIBUN FOOD CHEMIFA; trade name "Hyaluronic acid FCH") dissolved in 3L of distilled water was heated to 40° C. The solution was adjusted to pH 6.0 with 0.1 M aqueous sodium hydroxide solution, and then a hyaluronidase derived from Streptomyces hyalurolyticus (a product of Amano Pharmaceutical; trade name "Hyaluronidase "Amano"") was added to decrease 1 turbidity unit per mg of sodium hyaluronate, and the mixed solution was reacted for 100 hours at 40° C. After the reaction, the enzyme was removed from the solution by an ultrafiltration membrane (a product of Millipore) of hydrophilic polyethersulfone with a nominal molecular weight cutoff of 10k. The solvent was removed by lyophilization to give a depolymerization product (53.7 g).

The depolymerization product was fractionated by anion exchange chromatography (column: TSKgel DEAE-5PW, eluent A: water, B: aqueous solution of 0.5M sodium acetate; linear gradient (A/B (90/10) A/B (60/40); 40 min), detection: UV (232 nm)) (Compound Examples 1 and 2 were eluted in this order) to obtain fractions containing Compound Examples 1 and 2. Each fraction was lyophilized to remove water. Each lyophilized fraction was desalted by washing with ethanol to give Compound Examples 1 and 2 (white powder). Yields: Compound Example 1: 18.1 g, Compound Example 2: 29.5 g. Each compound was obtained as a sodium salt.

The purity of each compound measured by high performance liquid chromatography (column: TSKgel Amide-80, eluent: acetonitrile/water/acetic acid/triethylamine (65/35/2/1, v/v), flow velocity: 1.0 mL/min, column temperature: 80° C., detection: UV (232 nm); area percentage method) was 97% or more. The uronic acid content and hexosamine content analyzed by the methods shown in Example 1 nearly agreed with the theoretical values.

Example 3

Compound Production Example 3

Production of 4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranitol [ΔHexA β1→3GlcNAc β1→4GlcA β1→3GlcNAc OH (Compound Example 5)], and 4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(13)-O-2-acetamide-2-deoxy-β-D-glucopyranosyl-(1→4)-3-O-β-D-glucopyranuronosyl-(1→3)-O-2-acetamide-2-deoxy-β-D-glucopyranitol [ΔHexA β1→3GlcNAc β1→4GlcA β1→3GlcNAc β1→4GlcA β1→3GlcNAc OH (Compound Example 6)]

A solution of 50 mg of Compound Example 1 dissolved in 50 mL of an aqueous solution of 3 mg/mL sodium borohydride was treated for 1 hour at room temperature. The reaction was quenched with 5 mL of 6 M acetic acid and 50 mL of methanol was added, and then the mixture was dried on an evaporator. The addition of 50 mL methanol and evaporation were further repeated twice. The solid remaining after evaporation was dissolved in 5 mL of water and the solution was desalted by gel filtration in the same manner as in Example 1, and then lyophilized to give Compound Example 5 (white powder: 44.7 mg).

In the same manner. Compound Example 6 was obtained using Compound Example 2 as the starting material.

Compound Examples 5 and 6 are represented by formula (21) where n denotes an integer of 1 to 2, i.e., n is 1 and 2, respectively.

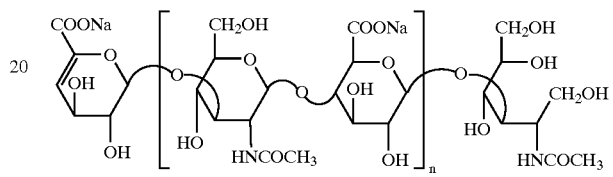

Formula (21)

The purity of each of Compound Nos. 5 and 6 measured by the method shown in Example 2 was 98% or higher. The uronic acid content and hexosamine content analyzed by the methods shown in Example 1 nearly agreed with the theoretical values.

Example 4

Compound Production Example 4

Production of 4-deoxy-α-L-threo-hexa-4-enepyranuronosyl-(1–3)-O-2-acetamide-2-deoxy-β-D-glucopyranosyl-(1→4)-3-O-β-D-glucopyranuronic acid [ΔHexA β1→3GlcNAc β1→4GlcA (Compound Example 7)], and 4-deoxy-α-L-threo-hexa-4-enepyranuronosyl-(1–3)-O-2-acetamide-2-deoxy-β-D-glucopyranosyl-(1–4)-3-O-β-D-glucopyranuronosyl-(13)-O-2-acetamide-2-deoxy-β-D-glucopyranosyl-(1→4)-3-O-β-D-glucopyranuronic acid [ΔHexA β1→3GlcNAc β1→4GlcA β1→3GlcNAc β1→4GlcA (Compound Example 8)]

Compound Example 1 was heated in a borate buffer at pH 9 in accordance with the method of Reissig et al. (Reissig, J., L., Strominger, J. L., Leloir, L., F.: J. Biol. Chem., 217, 959 (1953).). Boric acid in the reaction mixture was removed as methyl borate in the same manner as in Example 3. The remaining mixture was desalted by gel filtration in the same manner as in Example 1, and then lyophilized to obtain Compound Example 7 (white powder). Starting from 50 mg of Compound Example 1, 43.1 mg of Compound Example 7 was obtained.

Similarly, 44.8 mg of Compound Example 8 (white powder) was obtained starting from 50 mg of Compound Example 2.

Compound Examples 7 and 8 are represented by formula (22) where n denotes an integer of 0 to 1. i.e., n is 0 and 1, respectively.

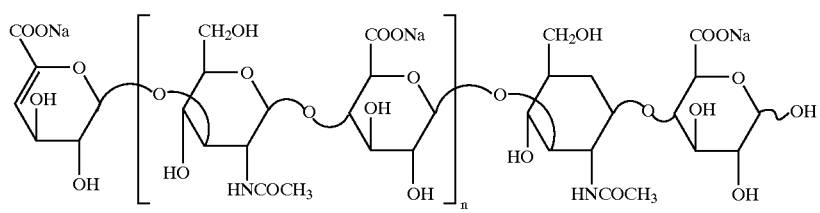

Formula (22)

The purity of each of Compound Examples 7 and 8 measured by the method shown in Example 2 was 98% or higher. The uronic acid content and hexosamine content analyzed by the methods shown in Example 1 nearly agreed with the theoretical values.

Example 5

Compound Production Example 5

Production of 4-deoxy-α-L-threo-hexa-4-enepyranuronosyl-(1→3)-O-2-acetamide-2-deoxy-β-D-glucopyranosyl-(1→4)-3-O-β-D-glucopyranuronitol [ΔHexA β1→3GlcNAc β1→4GlcA OH (Compound Example 9)], and 4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronitol [ΔHexA β1→3GlcNAc β1→4GlcA β1→3GlcNAc β1→4GlcA OH (Compound Example 10)]

Compound Example 7 was treated in the same manner as in Example 3 to give Compound Example 9 (white powder). Starting from 20 mg of Compound Example 7, 15.9 mg of Compound Example 9 was obtained.

Similarly, 17.8 mg of Compound Example 10 (white powder) was obtained starting from 20 mg of Compound Example 8.

Compound Examples 9 and 10 are represented by formula (23) where n denotes an integer of 0 to 1, i.e., n is 0 and 1, respectively.

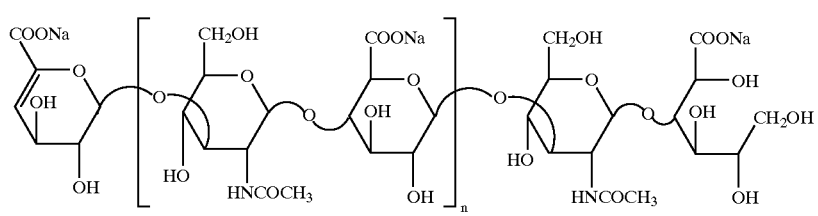

Formula (23)

The purity of each of Compound Nos. 9 and 10 measured by the method shown in Example 2 was 98% or higher. The uronic acid content and hexosamine content analyzed by the methods shown in Example 1 nearly agreed with the theoretical values.

Example 6

Sebum Production Inhibitory Effect of Compounds of Formula (1)

The method of Hall et al. (Hall, D. W. R., Van den Hoven, W. E., Noordzij-Kamermans, N. J., Jaitly, K. D., Arch. Dermatol. Res., 275, 1 (1983)) was followed. Namely, male hamster auricular skin tissue sections (3 mm in diameter) containing sebaceous glands were cultured for 3 hours in Krebs-Ringer phosphate buffer containing radioactively labeled sodium acetate, and then tissues were hydrolyzed and extracted with hexane. The radioactively labeled fat levels in hexane were measured in a liquid scintillation counter to determine fat production inhibition levels in sebaceous glands. Skin tissues isolated from the right auricula were cultured in Krebs-Ringer phosphate buffer containing 0.01% or 0.05% of compounds of the present invention (Compound Nos. 1–10) (compound systems), while skin tissues from the left auricula of the same hamster were cultured in Krebs-Ringer phosphate buffer containing no compounds of the present invention (control system). The sebum production inhibition percentage was calculated by the equation below from the test data obtained.

Sebum production inhibition (%)=[(Sebum production level in control system)−(Sebum production level in each compound system)]/(Sebum production level in control system)×100

The results are shown in Table 1.

TABLE 1

| | Sebum production inhibition (%) | |
| --- | --- | --- |
| | Concentration of compound in the medium (%) | |
| Compound No. | 0.01 | 0.05 |
| 1 | 15.7 | 17.8 |
| 2 | 28.6 | 50.1 |
| 3 | 48.5 | 47.7 |
| 4 | 53.4 | 51.0 |

TABLE 1-continued

| | Sebum production inhibition (%) Concentration of compound in the medium (%) | |
|---|---|---|
| Compound No. | 0.01 | 0.05 |
| 5 | 16.2 | 18.1 |
| 6 | 30.8 | 55.7 |
| 7 | 14.2 | 15.9 |
| 8 | 30.7 | 56.6 |
| 9 | 13.9 | 20.0 |
| 10 | 39.8 | 55.1 |

As shown in Table 1, all of Compound Nos. 1–10 were found to significantly inhibit fat production from skin tissue sections containing sebaceous glands and therefore have an excellent sebum production inhibitory effect.

Example 7

Acute Toxicity of Compounds of the Present Invention

Representative examples of compounds of the present invention (Compound Nos. 1–10) were tested for acute toxicity on rats (body weight 300–400 g, Wistar, male) to show $LD_{50}$ of 500 mg/kg or more.

Example 8

Preparation Example of Formulations and Cosmetics

| Preparation of tablet 1 | |
|---|---|
| Compound Example 1 | 10 g |
| Polyethylene glycol 6000 | 10 g |
| Sodium lauryl sulfate | 1.5 g |
| Corn starch | 3 g |
| Lactose | 25 g |
| Magnesium stearate | 0.5 g |

The above ingredients are weighed. Polyethylene glycol 6000 is heated to 70 to 80° C., and mixed with Compound Example 1, sodium lauryl sulfate, corn starch, and lactose, followed by cooling. The solidified mixture is granulated by means of a grinder to obtain granules. The granules are mixed with magnesium stearate, and then compressed into tablets with a weight of 250 mg.

| Preparation of tablet 2 | |
|---|---|
| Compound Example 2 | 30 g |
| Lactose | 55 g |
| Potato starch | 12 g |
| Polyvinyl alcohol | 1.5 g |
| Magnesium stearate | 1.5 g |

The above ingredients are weighed. Compound Example 2, lactose and potato starch are uniformly mixed. An aqueous solution of polyvinyl alcohol is added to the mixture, and the mixed solution is wet granulated. The resulting granules are dried and mixed with magnesium stearate. Then, the mixture is compressed into tablets with a weight of 200 mg.

| Preparation of capsule | |
|---|---|
| Compound Example 3 | 10 g |
| Lactose | 25 g |
| Corn starch | 5 g |
| Microcrystalline cellulose | 9.5 g |
| Magnesium stearate | 0.5 g |

The above ingredients are weighed. The four ingredients except magnesium stearate are uniformly mixed. Magnesium stearate is added, and then the ingredients are further mixed for several minutes. The mixture is filled into No. 1 hard capsule shells in an amount of 200 mg/capsule to form capsules.

| Preparation of powder | |
|---|---|
| Compound Example 4 | 20 g |
| Lactose | 79 g |
| Magnesium stearate | 1 g |

The above ingredients are weighed. All the ingredients are uniformly mixed to form a 20% powder.

| Preparation of suppository | |
|---|---|
| Compound Example 5 | 10 g |
| Polyethylene glycol 1500 | 18 g |
| Polyethylene glycol 4000 | 72 g |

Compound Example 2 is thoroughly ground in a mortar to form a fine powder, and made into a 1 g rectal suppository by a melting method.

| Preparation of injection | |
|---|---|
| Compound Example 6 | 0.1 g |
| Sodium chloride | 0.9 g |
| Sodium hydroxide | Suitable amount |
| Water for injection | 100 mL |

The above ingredients are weighed. The three ingredients are dissolved in water for injection, and the solution is sterilized by filtration. Then, the solution is dispensed into 10 mL ampoules in an amount of 5 mL per ampoule. The ampoule is heat sealed to form an injection.

| Preparation of cream | |
|---|---|
| Compound Example 7 | 5 g |
| Cetostearyl alcohol | 3.5 g |
| 2-Octyldodecyl alcohol | 3 g |
| Squalane | 40 g |
| Beeswax | 3 g |
| Reduced lanolin | 5 g |
| Ethylparaben | 0.3 g |
| Polyoxyethylene (20) sorbitan monopalmitate ester | 2 g |
| Monoglyceride stearate | 2 g |
| Perfume | 0.03 g |

-continued

| Preparation of cream | |
|---|---|
| 1,3-Butylene glycol | 5 g |
| Glycerin | 5 g |
| Purified water | 26.2 g |

The above ingredients are weighed and formulated into a cream by a standard procedure.

| Preparation of emulsion | |
|---|---|
| Compound Example 8 | 1 g |
| Liquid paraffin | 5 g |
| Stearic acid | 1.5 g |
| Cetyl alcohol | 0.5 g |
| Beeswax | 2 g |
| Isopropyl myristate | 3 g |
| Polyoxyethylene (10) monooleate ester | 1 g |
| Glyceryl monostearate ester | 1 g |
| Propylene glycol | 5 g |
| Ethanol | 3 g |
| Ethylparaben | 0.3 g |
| Perfume | 0.03 g |
| Purified water | 76.7 g |

The above ingredients are weighed and formulated into an emulsion by a standard procedure.

| Preparation of ointment | |
|---|---|
| Compound Example 9 | 0.1 g |
| Stearyl alcohol | 15 g |
| Japan wax | 20 g |
| Polyoxyethylene (10) monooleate ester | 0.25 g |
| Glyceryl monostearate ester | 0.25 g |
| Vaseline | 40 g |
| Purified water | 24.4 g |

The above ingredients are weighed and formulated into an ointment by a standard procedure.

| Preparation of pack | |
|---|---|
| Compound Example 10 | 7 g |
| Polyvinyl alcohol | 15 g |
| Dipropylene glycol | 5 g |
| Polyethylene glycol | 3 g |
| Ethanol | 10 g |
| Methylparaben | 0.05 g |
| Perfume | 0.05 g |
| Purified water | 59.9 g |

The above ingredients are weighed and formulated into a pack by a standard procedure.

| Preparation of pressed powder | |
|---|---|
| Compound Example 2 | 1 g |
| Talc | 85.4 g |
| Stearic acid | 1.5 g |
| Lanolin | 5 g |
| Squalane | 5 g |
| Sorbitan sesquioleate ester | 2 g |

-continued

| Preparation of pressed powder | |
|---|---|
| Triethanolamine | 1 g |
| Pigment | q.s. |
| Perfume | q.s. |

The above ingredients are weighed and formulated into a pressed powder by a standard procedure.

| Preparation of hair tonic | |
|---|---|
| Compound Example 3 | 1 g |
| Ethanol | 55 g |
| Nikkol HCO-60 | 1 g |
| Perfume | q.s. |
| Purified water | 42 g |
| Glycerin | 1 g |
| Dye | q.s. |

The above ingredients are weighed and formulated into a hair tonic by a standard procedure.

What is claimed is:

1. A method for treating a disease caused by excessive sebum production in a mammal, wherein said disease is acne vulgaris, said method comprising:

administering to said mammal presenting said disease a therapeutically effective amount of a sebum production inhibitor containing as an active ingredient a compound of general formula (1) below having a glucuronic acid derivative and a glucosamine derivative in the structure or a pharmacologically acceptable salt thereof, Formula (1)

$$\left[ R^9 - O \begin{array}{c} CH_2OR^8 \\ O \\ R^7O \\ NR^5R^6 \end{array} O \begin{array}{c} COOR^4 \\ O \\ OR^3 \\ OR^2 \end{array} R^1 \right]_n$$

where $R^1$ denotes a protective group or any of formulae (2) to (5) below where $R^{10}$ denotes a hydrogen atom, a protective group or any of formulae (6) to (8) below, and $R^{11}$ denotes a hydrogen atom or a protective group, provided that when $R^{10}$ and $R^{11}$ are a hydrogen atom or a protective group, R1 may be attached at the trans- or cis-position with respect to $COOR^4$,

| | |
|---|---|
| $-OR^{10}$ | Formula (2) |
| $-NHR^{11}$, | Formula (3) |
| $-CH_2R^{11}$ | Formula (4) |
| $-SR^{11}$, | Formula (5) |

Formula (6)

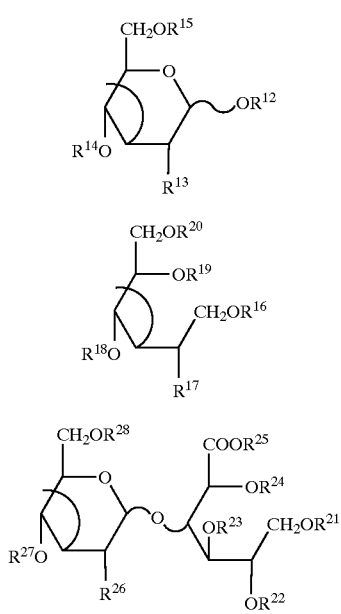

Formula (7)

Formula (8)

or when $R^{10}$ is any of formulae (6) to (8), $R^{12}$ to $R^{28}$ except $R^{13}$, $R^{17}$ and $R^{26}$ in formulae (6) to (8) are the same or different and denote a hydrogen atom or a protective group, and $R^{13}$, $R^{17}$ and $R^{26}$ denote an azido group or formula (9) below —$NR^{29}R^{30}$  formula (9)

where $R^{29}$ and $R^{30}$ are the same or different and denote a hydrogen atom or a protective group, $R^2$ to $R^4$ are the same or different and denote a hydrogen atom or a protective group, $R^9$ denotes formula (11) below Formula (11)

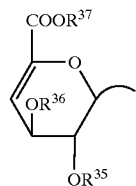

where $R^{35}$ to $R^{37}$ are the same or different and denote a hydrogen atom or a protective group, and n denotes an integer of 0 to 25, provided that when n is 0, $R^1$ is a group of formula (2) and $R^{10}$ is a group of formula (8), with the proviso that in formulae (1), (6) to (8), and (11), the protective groups are the same or different and denote an optionally substituted straight or branched alkyl having 1 to 8 carbon atoms, an optionally substituted straight or branched alkenyl having 2 to 8 carbon atoms, an optionally substituted acyl having 1 to 8 carbon atoms, an optionally substituted aromatic acyl, or an optionally substituted aromatic alkyl, or any two protective groups of $R^2$ to $R^{30}$ and $R^{35}$ to $R^{37}$ except $R^{13}$, $R^{17}$ and $R^{26}$ may be combined to form an optionally substituted alkylidene having 3 to 8 carbon atoms, an optionally substituted cyclic alkylidene having 3 to 8 carbon atoms, optionally substituted benzylidene or optionally substituted phthaloyl, and when n is 2 or more, $R^2$ to $R^8$ may be the same or different in each recurring unit, and a pharmaceutically acceptable carrier.

2. A method for treating dandruf in a mammal, said method comprising:

administering to said mammal a therapeutically effective amount of a sebum production inhibitor containing as an active ingredient a compound of general formula (1) below having a glucuronic acid derivative and a glucosamine derivative in the structure or a pharmacologically acceptable salt thereof, Formula (1)

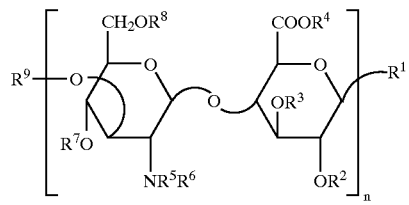

where $R^1$ denotes a protective group or any of formulae (2) to (5) below where $R^{10}$ denotes a hydrogen atom, a protective group or any of formulae (6) to (8) below, and $R^{11}$ denotes a hydrogen atom or a protective group, provided that when $R^{10}$ and $R^{11}$ are a hydrogen atom or a protective group, R1 may be attached at the trans- or cis-position with respect to $COOR^4$, —$OR^{10}$  Formula (2)

—$NHR^{11}$,  Formula (3)

—$CH_2R^{11}$,  Formula (4)

—$SR^{11}$,  Formula (5)

Formula (6)

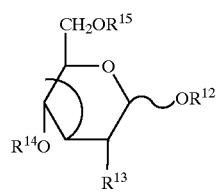

Formula (7)

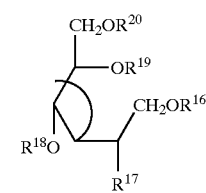

Formula (8)

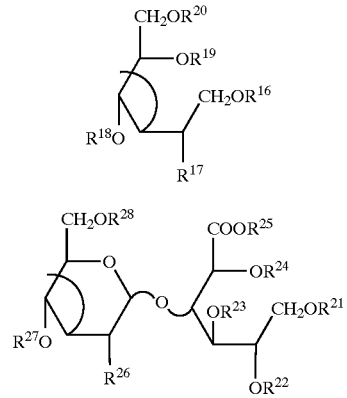

or when $R^{10}$ is any of formulae (6) to (8), $R^{22}$ to $R^{28}$ except $R^{13}$, $R^{17}$ and $R^{26}$ in formulae (6) to (8) are the same or different and denote a hydrogen atom or a protective group, and $R^{13}$, $R^{17}$ and $R^{26}$ denote an azido group or formula (9) below

 formula (9)

where $R^{29}$ and $R^{30}$ are the same or different and denote a hydrogen atom or a protective group, $R^2$ to $R^8$ are the same or different and denote a hydrogen atom or a protective group, $R^9$ denotes formula (11) below

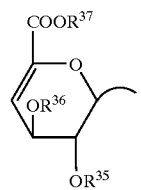

Formula (11)

where $R^{35}$ to $R^{37}$ are the same or different and denote a hydrogen atom or a protective group, and n denotes an integer of 0 to 25, provided that when n is 0, $R^1$ is a group of formula (2) and $R^{10}$ is a group of formula (8), with the proviso that in formulae (1), (6) to (8), and (11), the protective groups are the same or different and denote an optionally substituted straight or branched alkyl having 1 to 8 carbon atoms, an optionally substituted straight or branched alkenyl having 2 to 8 carbon atoms, an optionally substituted acyl having 1 to 8 carbon atoms, an optionally substituted aromatic acyl, or an optionally substituted aromatic alkyl, or any two protective groups of $R^2$ to $R^{30}$ and $R^{35}$ to $R^{37}$ except $R^{13}$, $R^{17}$ and $R^{26}$ may be combined to form an optionally substituted alkylidene having 3 to 8 carbon atoms, an optionally substituted cyclic alkylidene having 3 to 8 carbon atoms, optionally substituted benzylidene or optionally substituted phthaloyl, and when n is 2 or more, $R^2$ to $R^8$ may be the same or different in each recurring unit, and a pharmaceutically acceptable carrier.

3. A method for treating body odor associated with aging in a mammal, said method comprising:

administering to said mammal a therapeutically effective amount of a sebum production inhibitor containing as an active ingredient a compound of general formula (1) below having a glucuronic acid derivative and a glucosamine derivative in the structure or a pharmacologically acceptable salt thereof, Formula (1)

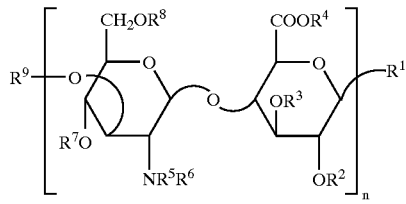

where $R^1$ denotes a protective group or any of formulae (2) to (5) below where $R^{10}$ denotes a hydrogen atom, a protective group or any of formulae (6) to (8) below, and $R^{11}$ denotes a hydrogen atom or a protective group, provided that when $R^{10}$ and $R^{11}$ are a hydrogen atom or a protective group, R1 may be attached at the trans- or cis-position with respect to $COOR^4$,

 Formula (2)

 Formula (3)

 Formula (4)

 Formula (5)

Formula (6)

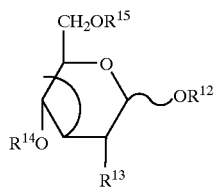

Formula (7)

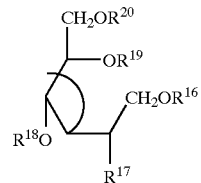

Formula (8)

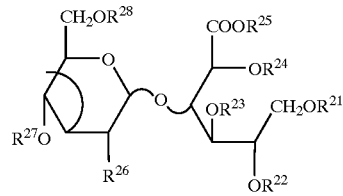

or when $R^{10}$ is any of formulae (6) to (8), $R^{12}$ to $R^{28}$ except $R^{13}$, $R^{17}$ and $R^{26}$ in formulae (6) to (8) are the same or different and denote a hydrogen atom or a protective group, and $R^{13}$, $R^{17}$ and $R^{26}$ denote an azido group or formula (9) below

 formula (9)

where $R^{29}$ and $R^{30}$ are the same or different and denote a hydrogen atom or a protective group, $R^2$ to $R^8$ are the same or different and denote a hydrogen atom or a protective group, $R^9$ denotes formula (11) below Formula (11)

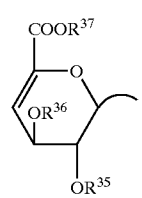

where $R^{35}$ to $R^{37}$ are the same or different and denote a hydrogen atom or a protective group, and n denotes an integer of 0 to 25, provided that when n is 0, $R^1$ is a group of formula (2) and $R^{10}$ is a group of formula (8), with the proviso that in formulae (1), (6) to (8), and (11), the protective groups are the same or different and denote an optionally substituted straight or branched

23 alkyl having 1 to 8 carbon atoms, an optionally substituted straight or branched alkenyl having 2 to 8 carbon atoms, an optionally substituted acyl having 1 to 8 carbon atoms, an optionally substituted aromatic acyl, or an optionally substituted aromatic alkyl, or any two protective groups of $R^2$ to $R^{30}$ and $R^{35}$ to $R^{37}$ except $R^{13}$, $R^{17}$ and $R^{26}$ may be combined to form an optionally substituted alkylidene having 3 to 8 carbon atoms, an optionally substituted cyclic alkylidene having 3 to 8 carbon atoms, optionally substituted benzylidene or optionally substituted phthaloyl, and when n is 2 or more, $R^2$ to $R^8$ may be the same or different in each recurring unit, and a pharmaceutically acceptable carrier.

4. A method for treating an oily skin condition caused by excessive sebum production in a mammal, wherein said oily skin condition is rough skin, shiny skin, greasy skin or greasy hair, said method comprising administering to said mammal presenting said oily skin condition a therapeutically effective amount of a sebum production inhibitor containing as an active ingredient a compound of general formula (1) below having a glucuronic acid derivative and a glucosamine derivative in the structure or a pharmacologically acceptable salt thereof, Formula (1)

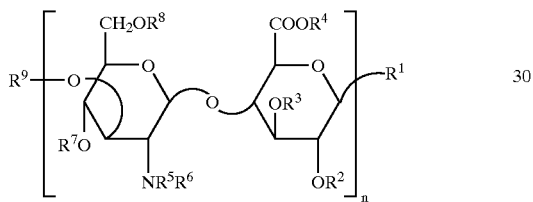

where $R^1$ denotes a protective group or any of formulae (2) to (5) below where $R^{10}$ denotes a hydrogen atom, a protective group or any of formulae (6) to (8) below, and $R^{11}$ denotes a hydrogen atom or a protective group, provided that when $R^{10}$ and $R^{11}$ are a hydrogen atom or a protective group, R1 may be attached at the trans- or cis-position with respect to $COOR^4$, —$OR^{10}$      Formula (2)

—$NHR^{11}$,      Formula (3)

—$CH_2R^{11}$,      Formula (4)

—$SR^{11}$,      Formula (5)

Formula (6)

Formula (7)

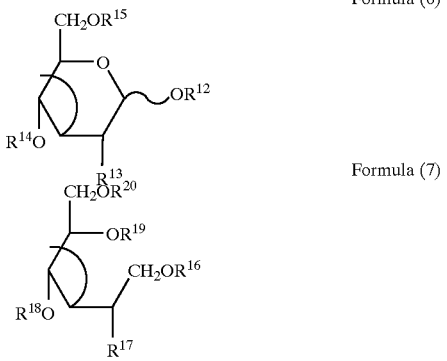

24

Formula (8)

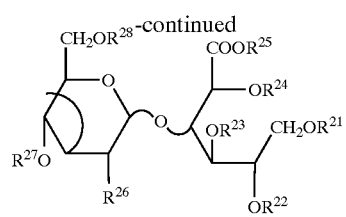

or when $R^{10}$ is any of formulae (6) to (8), $R^{12}$ to $R^{28}$ except $R^{13}$, $R^{17}$ and $R^{26}$ in formulae (6) to (8) are the same or different and denote a hydrogen atom or a protective group, and $R^{13}$, $R^{17}$ and $R^{26}$ denote an azido group or formula (9) below —$NR^{29}R^{30}$      formula (9)

where $R^{29}$ and $R^{30}$ are the same or different and denote a hydrogen atom or a protective group, $R^2$ to $R^8$ are the same or different and denote a hydrogen atom or a protective group, $R^9$ denotes formula (11) below Formula (11)

where $R^{35}$ to $R^{37}$ are the same or different and denote a hydrogen atom or a protective group, and n denotes an integer of 0 to 25, provided that when n is 0, $R^1$ is a group of formula (2) and $R^{10}$ is a group of formula (8), with the proviso that in formulae (1), (6) to (8), and (11), the protective groups are the same or different and denote an optionally substituted straight or branched alkyl having 1 to 8 carbon atoms, an optionally substituted straight or branched alkenyl having 2 to 8 carbon atoms, an optionally substituted acyl having 1 to 8 carbon atoms, an optionally substituted aromatic acyl, or an optionally substituted aromatic alkyl, or any two protective groups of $R^2$ to $R^{30}$ and $R^{35}$ to $R^{37}$ except $R^{13}$, $R^{17}$ and $R^{26}$ may be combined to form an optionally substituted alkylidene having 3 to 8 carbon atoms, an optionally substituted cyclic alkylidene having 3 to 8 carbon atoms, optionally substituted benzylidene or optionally substituted phthaloyl, and when n is 2 or more, $R^2$ to $R^8$ may be the same or different in each recurring unit, and a pharmaceutically acceptable carrier.

5. The method according to any one of claims 1, 2, 3, or 4, wherein said carrier is selected from the group consisting of a diluent, an aerosol, a topical carrier, an aqueous solution, a nonaqueous solution, and a solid carrier.

6. The method according to any one of claims 1, 2, 3 or 4, wherein said mammal is a human.

* * * * *